(12) United States Patent
Heller et al.

(10) Patent No.: US 8,738,125 B1
(45) Date of Patent: May 27, 2014

(54) DEVICES AND METHODS FOR DELIVERING MOLECULES TO THE HEART WITH ELECTRIC FIELDS

(75) Inventors: Richard Heller, Temple Terrace, FL (US); William Marshall, Lakeland, FL (US); Mark J. Jaroszeski, Wesley Chapel, FL (US)

(73) Assignee: University of South Florida, Tampa, FL (US)

(*) Notice: Subject to any disclaimer, the term of this patent is extended or adjusted under 35 U.S.C. 154(b) by 678 days.

(21) Appl. No.: 12/059,068

(22) Filed: Mar. 31, 2008

Related U.S. Application Data

(60) Provisional application No. 60/909,257, filed on Mar. 30, 2007.

(51) Int. Cl.
*A61N 1/30* (2006.01)

(52) U.S. Cl.
USPC .......................................................... 604/21

(58) Field of Classification Search
USPC ............... 604/20, 21; 607/115, 116, 119–122
See application file for complete search history.

(56) References Cited

U.S. PATENT DOCUMENTS

| | | | |
|---|---|---|---|
| 5,403,311 A * | 4/1995 | Abele et al. ..................... 606/49 |
| 5,944,710 A | 8/1999 | Dev et al. | |
| 6,219,577 B1 | 4/2001 | Brown, III et al. | |
| 6,241,701 B1 | 6/2001 | Hofmann | |
| 6,865,416 B2 | 3/2005 | Dev et al. | |
| 7,127,284 B2 | 10/2006 | Seward | |
| 7,742,809 B2 * | 6/2010 | Sigg et al. ...................... 604/20 |
| 2003/0120208 A1 | 6/2003 | Houser et al. | |
| 2003/0220676 A1 * | 11/2003 | Helland ....................... 607/122 |
| 2005/0049542 A1 | 3/2005 | Sigg et al. | |
| 2006/0184092 A1 | 8/2006 | Atanasoska et al. | |
| 2009/0254019 A1 * | 10/2009 | Gehl et al. ...................... 604/21 |

OTHER PUBLICATIONS

Loree C. Heller, Kenneth Ugen, and Richard Heller. 2005. "Electroporation for targeted gene transfer." Ashley Publications. pp. 1-14. 2005.
B. Mali, T. Jarm, F. Jager, and D. Miklavcic. 2005. "An algorithm for synchronization of in vivo electroporation with ECG." Journal of Medical Engineering and Technology. vol. 29. No. 6. Nov./Dec. 2005. pp. 288-296.
Dev NB, Preminger TJ, Hofmann GA, Dev SB. "Sustained local delivery of heparin to the rabbit arterial wall with an electroporation catheter." Cathet Cardiovasc Diagn. Nov. 1998 vol. 45. No. 3. pp. 337-345.

* cited by examiner

*Primary Examiner* — Bhisma Mehta
*Assistant Examiner* — Bradley Osinski
(74) *Attorney, Agent, or Firm* — Michele L. Lawson; Michael McGaw; Smith & Hopen, P.A.

(57) ABSTRACT

A device and related methodologies to deliver molecules to the cells that comprise any tissues. The invention includes a catheter-based electrode and methods for its use for the delivery of molecules to cardiac tissue, blood vessels, other tissues/organs that can be accessed through a luminal tissue, and luminal tissues. The invention is also a non-catheter based electrode for performing the same functions. In certain embodiments the electrode utilizes a segmented electrode array wherein each electrode is separately addressable by a source of electricity.

22 Claims, 2 Drawing Sheets

DEVICES AND METHODS FOR DELIVERING MOLECULES TO THE HEART WITH ELECTRIC FIELDS

CROSS REFERENCE TO RELATED APPLICATIONS

This application claims priority to U.S. Provisional Patent Application 60/909,257, entitled, "Devices and Methods for Delivering Molecules to the Heart with Electric Fields", filed Mar. 30, 2007, the contents of which are herein incorporated by reference.

FIELD OF INVENTION

This invention relates to drug delivery devices. More specifically, this invention relates electrically-mediated delivery of molecules to cells.

BACKGROUND OF THE INVENTION

Electroporation ("EP") originated for in vitro transfection (Neumann et al., 1982) and over the past 25 years has become a standard laboratory method. The administration of electric fields at specific pulse conditions increases cell membrane permeability, which allows uptake of molecules through the cell membrane. The initial demonstration of in vivo electroporation was the delivery of chemotherapeutic agents to solid tumors (Okino et al. 1991). In the mid to late 1990's, the effectiveness of this approach for drug delivery was demonstrated in a variety of different tumors in animals and humans (Gotheif et al, 2003). This technique was then tested for enhanced plasmid DNA delivery (Holler et al., 1996; Nishi et al, 1996). In vivo electroporation is theoretically applicable to all tissues tested. A principal issue limiting the use of in vivo electroporation has been the accessibility of the particular tissue for the application of the electric field. The use of in vivo electroporation for plasmid DNA deliver has seen tremendous growth, including the initiation of the first clinical trials.

Treatment of the tissue site by localized delivery of the therapeutic agent coupled with focused delivery of the electroporation signal facilitates selective application of the treatment to the target tissue sought to be treated. In this manner surrounding tissue is spared the adverse effects of treatment while the targeted tissue receives enhanced more optimal levels of the agent.

Plasmid DNA-based gene transfer is attractive because it eliminates the need for a biological vector. Application of plasmid DNA-based gene transfer has been handicapped by the lack of efficient and/or effective delivery methods. When compared to viral delivery, the advantages of plasmid DNA-based gene transfer include reduced potential for immunogenicity, integration into the genome, and environmental spread. One method that has emerged as a means to facilitate delivery of plasmid DNA is in vivo electroporation or electropermeabilization.

SUMMARY OF INVENTION

The present invention provides devices and methods to deliver molecules to the cells that comprise any tissues. In certain embodiments the invention provides a catheter-based electrode and methods for its use for the delivery of molecules to cardiac tissue, blood vessels, other tissues/organs that can be accessed through a luminal tissue and luminal tissues. In additional embodiments the invention provides a non-catheter based electrode for performing the same functions.

An injection and electroporation delivery device according to the invention can be fitted on the tip of a catheter to access and treat tissues that can be accessed using tissues that have a lumen. The heart provides an example of a tissue can be accessed using a catheter with this device on the tip through any number of blood vessels that lead to it. Similarly, kidney, lung, pancreas, liver, gall bladder, urinary bladder, prostate, and stomach can be accessed and treated using the device mounted on the tip of a catheter. The diameter of the device can be tailored to any size that is suitable for accessing the tissue of interest.

In addition, the device can be used to treat the luminal pathway itself. One advantage of the system described herein is that it does not rely on balloon-based systems, as do many of the catheter based electrodes for treating vessels. Moreover, the device can be used in a non-expandable format.

In a first aspect the present invention provides a catheter-based electroporation device. The device includes a catheter body, a guide disposed within the catheter, a retractable needle disposed within the lumen of the guide, and at least one electrode affixed to the distal tip of the catheter body. The guide has an elongate tubular body defining an inner lumen and serves to guide the needle. The needle has a distal tip with an aperture to allow the fluid to exit the tip of the needle. By exiting the tip through the aperture, the agent is delivered to the site of electroporation. Where there are a plurality of electrodes in the catheter-based electroporation device, each electrode can be independently addressable by a source of electricity. This provides an added element of control over the application of the electric field generated between the electrodes. Alternatively, the needle and each electrode of the at least one of electrode is independently addressable by a source of electricity.

In certain embodiments of the electroporation device the electrode utilizes a plurality of segmented electrodes arrayed on the distal tip of the catheter body. The plurality of segmented electrodes are electrically insulated from adjacent electrodes, thus preventing interference. The plurality of segmented electrodes can be substantially equidistantly arrayed on the distal tip of the catheter body. By knowing and/or controlling the spacing, the electric field generated for a given applied voltage can be controlled. The electroporation device can employ needles composed of an electrically conductive material and can have a proximal end comprising a connector to couple the needle to a source of electricity. Further, each of the electrodes and the needle can be independently addressable by a source of electricity. The electroporation device can also employ a plurality of needles. Each of the plurality of needles can be adapted to deliver a different agent. Furthermore, each of the plurality of needles can be composed of an electrically conductive material and have proximal end comprising a connector to couple the needle to a source of electricity. Additionally, each of the at least electrodes and each of the needles can be independently addressable by a source of electricity.

In a second aspect the present invention provides an electroporation device including a guide, a retractable needle disposed within the inner lumen of the guide, and at least one electrode affixed on or adjacent to the distal tip of the guide and spaced apart from needle by a predetermined space. The guide has an elongate tubular body defining an inner lumen. The needles are composed of an electrically conductive material and have a proximal end with a connector to couple the needle to a source of electricity. Each of the electrodes and the needle can be independently addressable by a source of source of electricity.

In certain embodiments at least one electrode comprises a plurality of segmented electrodes substantially equidistantly arrayed on the distal tip of the guide. The needle can utilize a distal tip with an aperture to allow a fluid to exit the tip of the needle thereby delivering the agent to the site of electroporation. In further embodiments can include a catheter body where the electrodes are affixed to the tip of the catheter body and the guide is disposed with the catheter body. The device can also include a connector to connect the device to an instrument. The instrument can include a catheter, an endoscope, or a bronchoscope. Alternatively, the device can include a connector to connect the device to a handle or a probe adapted for surgical treatment. The needle can be a plurality of needles, rather than a single needle, with each needle independently addressable by a source of electricity.

In a third aspect the present invention provides an electroporation device including a guide having an elongate tubular body defining an inner lumen and a plurality of segmented electrodes affixed on or adjacent to the distal tip of the guide. Each segment of the segmented electrodes can be spaced apart from adjacent electrodes by a predetermined space, with each of the electrodes independently addressable by a source of source of electricity.

In certain embodiments the electroporation device has a retractable needle disposed within the inner lumen of the guide. The needle can be composed of an electrically conductive material and have a connector to couple the needle to a source of electricity. The needle can also have a distal tip with an aperture to allow a fluid to exit the tip of the needle. Rather than employing a single needle, there can be a plurality of needles, with each needle independently addressable by a source of electricity.

In certain embodiments the electroporation device can include a catheter body. The electrodes can be affixed to the tip of the catheter body and the guide can be disposed within the catheter body. In further embodiments the electroporation device can include a connector to connect the device to an instrument. The instrument can be a catheter, an endoscope, or a bronchoscope. Alternatively, the device can include a connector to connect the device to a handle or probe adapted for surgical treatment.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

The invention provides an injection and electroporation delivery device. In certain embodiments the device can be fitted on the tip of a catheter. The device facilitates the access and treatment of tissues that can be accessed via a lumen. In particular, the device allows a therapeutic and/or diagnostic agent or other molecule to be injected into a tissue having a cell or cells sought to be treated with the agent or molecule. The invention is described below in examples which are intended to further describe the invention without limitation to its scope.

Example 1

Figure 1:
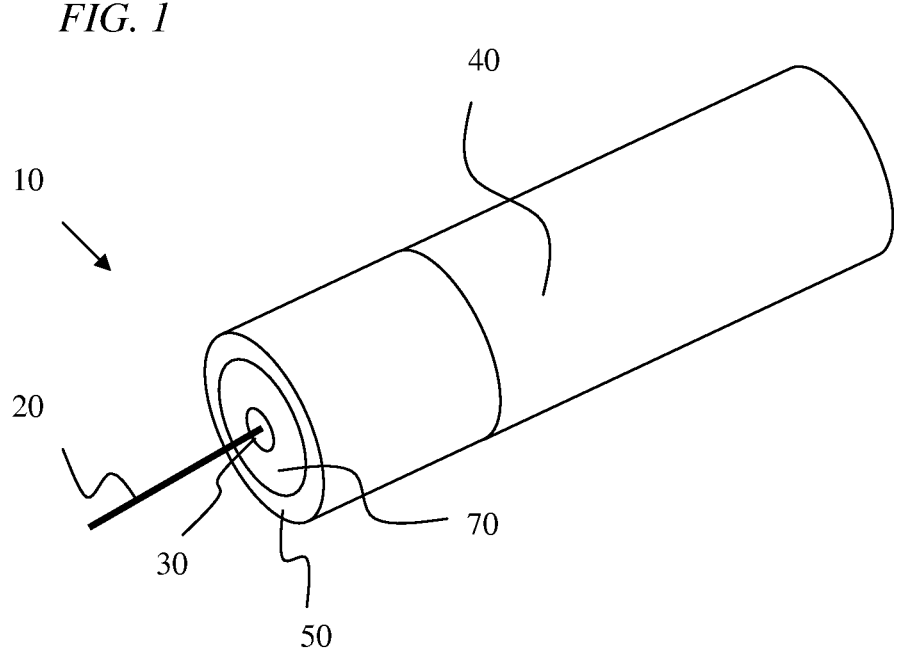
FIG. 1 is an illustration of the tip of a catheter according to an aspect of the present invention having a continuous metal end and retractable metal central needle for injecting molecules into tissues. The metal end has an independent path to a source of electricity and the needle has an independent connection to a source of electricity.

FIG. 1 shows an exemplary embodiment of an electroporation device 10 according to the present invention. The electroporation device 10 is integral with a catheter 40. The body of the catheter 40 can be multilayered, but should be coated with, or have peripheral layers composed of, a nonconductive material. The electroporation device 10 includes an electrode 50 that consists of a metal tip that covers the entire distal end of the catheter 40. While described above as being metal, the electrode 50 can fabricated of any sufficiently conductive material. The metal tip electrode 50 has an independent pathway to an electrical power source. The exemplary device also includes a central metal needle 20 disposed within the lumen of the catheter 40. As with the electrode 50, the needle 20 is described as being metal, but can be fabricated of any conductive material. The needle 20 can be extended and retracted through a hole in the tip of the catheter 40. The central needle 20 facilitates the injection of a molecule into a tissue and also serves as an electrode. The needle 20 has an independent pathway to an electrical power source (i.e. independent to the pathway of the electrode 50).

Figure 2:
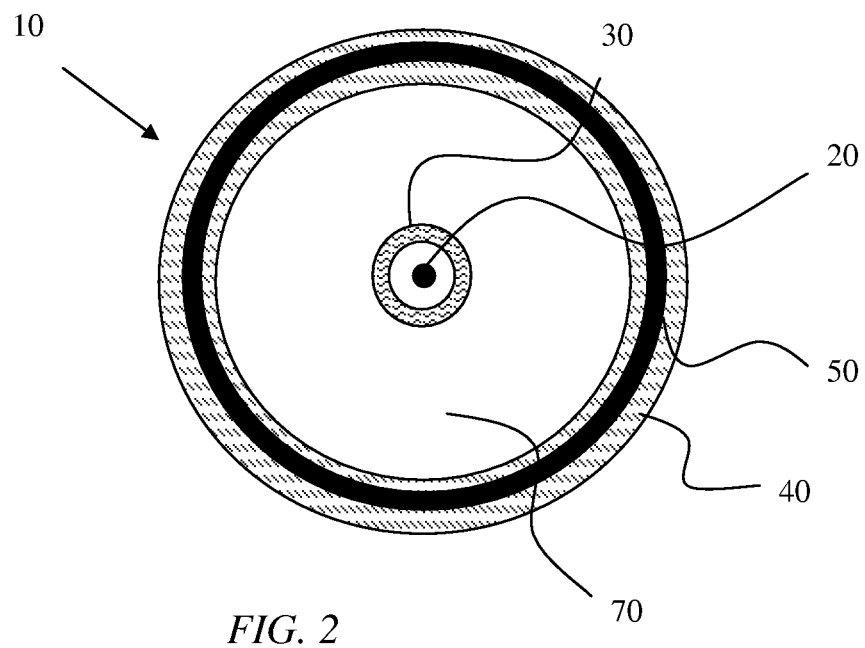
FIG. 2 is an alternative illustration of the catheter tip of FIG. 1, showing a cross-sectional view of the device.

The electroporation device 10 includes a guide 30 which aides in the disposition of the needle 20 including during the extension and retraction of the needle 20. The guide 30 generally is tubular, providing an additional lumen within the lumen of the catheter 40. Depending upon the application, the guide 30 may be conductive or nonconductive. As an alternative to having a conductive needle 20 attached to a source of electricity, the guide 30 could composed of a conductive material and connected independently to a source of electricity. With the catheter 40 in place within a lumen of the patient, the needle 20 is able to extend towards the tissue to be treated via the guide 30. The needle 20 may be hollow or solid. Where the needle 20 is hollow, it may include an aperture at the distal end of the needle and be used to deliver the agent to the tissue. Alternatively, the agent may be delivered such as through the guide 30. The distal end of the needle 20 may be sharp or blunt depending upon the particular application. The space 70 between the inner wall of the catheter 40 and the catheter and the outer wall of the guide 30 can comprise an insulating and/or nonconductive material. Alternatively, the space 70 may be empty or filled with air. FIG. 2 shows a cross-sectional view of the distal end of the electroporation device 10.

Electrical treatment is administered by passing electricity between the electrodes (needle 20 and metal tip electrode 50). The device 10 would be used by first inserting the device 10 integral with the catheter 40 into an organ that has a lumen such as a peripheral blood vessel, coronary arteries, or interior of the heart. The needle 20 would be extended so that it protrudes into a tissue, and a quantity of molecules would be injected into the tissue. The metal tip electrode 50 would be positioned so that it is near the injection site. Electrical treatment would be applied between the needle 20 and metal tip electrode 50 to deliver molecules to the interior of the cells that comprise the tissue by electroporation. Molecular delivery is just one application of the device. It can be used to manipulate molecules in any manner in or near the tissue.

Example 2

Segmented Tip

Figure 3:
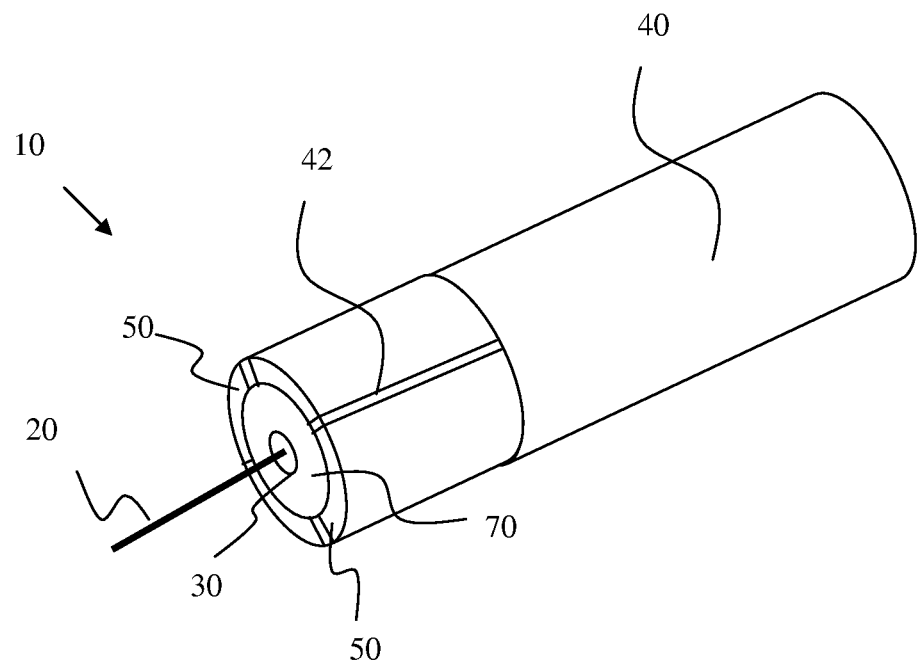
FIG. 3 is an illustration of the tip of a catheter according to another aspect of the present invention having a segmented metal end and a retractable metal central needle injecting molecules into tissues. The segments of the metal end each have an independent path to a source of electricity, and the needle also has an independent connection to a source of electricity. Alternatively, the needle may not have an independent path to a source of electricity and also may be made of a nonconductive material or insulated so that it does not influence electrical treatment.
Figure 4:
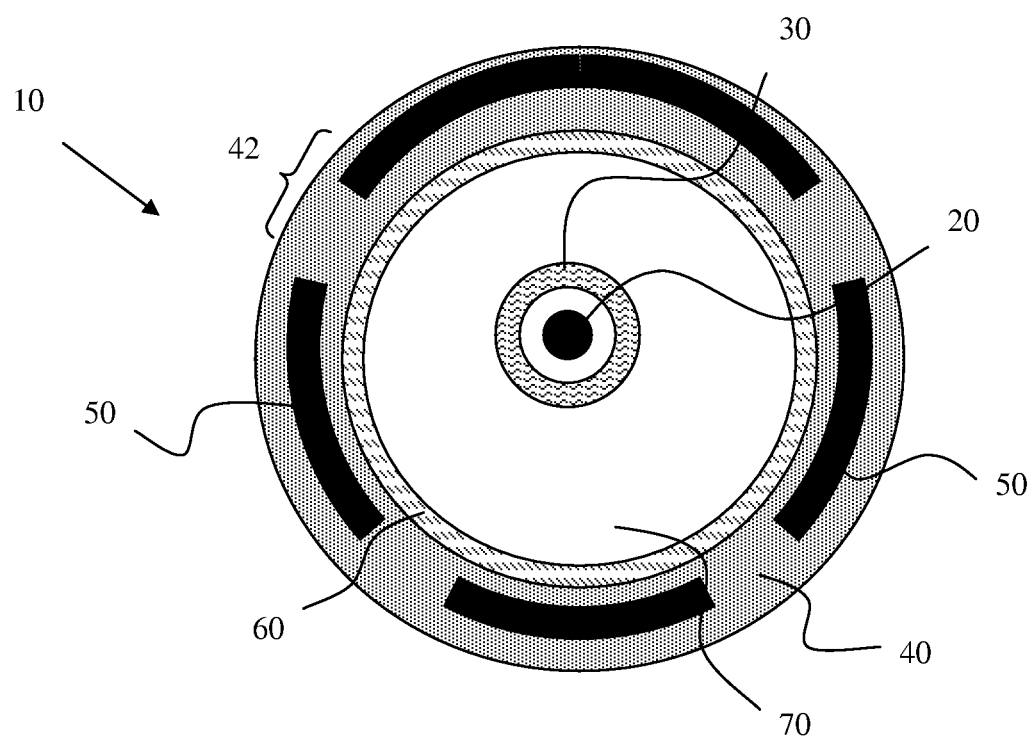
FIG. 4 is an alternative illustration of the catheter tip of FIG. 3, showing a cross-sectional view of the device.

FIG. 3 shows an alternative embodiment of an electroporation device 10. The embodiment shows the electroporation device 10 with a segmented tip electrode array 50 at the distal end of a catheter 40. The metal tip electrode array 50 consists of any number of segments that each have an independent path to a source of electricity. The number of segments can range from 2 to infinity (for example, there could be 2, 3, 4, 5, 6, 7, 8, 9, 10, 11, 12 or more segmented electrodes in conjunction with the needle, which may also be independently coupled to a source of electricity). Each segment is electrically insulated 42 from adjacent segments. Each segment of the segmented tip electrode array 50, along with the needle if the needle is attached to a source of electricity. As above, the array 50 is referred to a metal tip, but the segments of the electrode array 50 can be constructed of any electrically conductive material. Furthermore each segment of the electrode array 50 is independently addressable by the source of electricity, thus allowing a user to select which segment or segments (including the needle 20 where the needle is connected to a source of electricity) will participate in the generation of the electric field in a particular treatment. Furthermore, all segments may be simultaneously addressed depending upon the particular needs. One advantage of the independently addressable array of segments is that it gives a user better control over the applied fields, with benefit seen in subsequent expression of DNA or delivery of drugs. A central retractable needle 20 can be used to administer molecules into a target tissue as indicated above. The needle 20, if connected to a source of electricity, can be constructed from any electrically conductive material. The central needle 20 has an independent path to an electricity source when used in electroporation. This particular embodiment can be utilized by applying an electrical potential, or current, between at least one segment of the electrode array 50 to the needle 20. Alternatively, electricity can be applied between two or more segments of the electrode array 50. In alternate embodiments, the central needle 50 is not used as an electrode, is not made of an electrically conductive material, is electrically insulated, or is retracted into the catheter so that it will not influence the electrical treatment occurring at the segments of the metal tip. In still further embodiments, the device includes a plurality of needles, disposed within the same guide or in separate guides, and may further be insulated from adjacent needles. Alternatively, microneedles may be employed for the delivery of the agent. Where there are a plurality of needles, each needle can be coupled independently to a source of electricity. The needles in the plurality not being used can be retracted to assure that they will not interfere with treatment. Separate needles in the plurality can then be used to deliver different agents to the tissue.

The arrangement of electrodes and needles shown in FIGS. 1 through 4 can be used in further embodiments that are functionally identical with respect to the needle and electrodes. These embodiments include a device with the same relative orientation of electrodes and needles that is not attached to a catheter but are attached to a handle. These types of devices could be used for any tissue type, during open laparotomy thoracotomy, sternotomy, or during procedures using endoscopes.

An additional embodiment is the general use of electric fields in cardiac muscle to deliver molecules to the cells that comprise the tissue, remove molecules from the cells that comprise cardiac tissue, or manipulate molecules in the extracellular space of cardiac tissue.

The embodiments present above could be adapted for use in any type of minimally invasive technique that includes the use of catheters, endoscopes, bronchoscopes, as well as laparoscopic and thoracoscopic techniques.

The embodiments presented above can be used to treat any disease in any tissue in humans or animals using minimally invasive methods, open laparotomy, thoracotomy, sternotomy, or when no surgical or other procedures are required to access the treatment site (for example, skin). Some examples of diseases that could be treated using the embodiments include, but are not limited to, re-stenosis in blood vessels including coronary vessels, cardiac ischemia, peripheral vascular disease, peripheral artery disease, lung cancer, colon cancer, prostate cancer, breast cancer, skin cancer, bladder cancer, liver cancer, brain cancer, and any cancer of the GI tract.

Numerous ways of practicing the invention described in this application are possible. These include, but are not limited to, using the described devices to cause: (1) movement of molecules in the extra-cellular space; (2) movement of molecules from the extra-cellular space through the barrier surrounding a living cell, such as the cell membrane, and into the cell; (3) movement of molecules within the cell interior; (4) movement of molecules from the cell interior through the barrier surrounding a living cell and into the extracellular space; (5) a change in the properties of the barrier surrounding a living cell to make it more permeable to exogenous molecules; (6) movement of molecules into the barrier surrounding a living cell; (7) movement of molecules in a nonliving matrix; (8) movement of cells in a medium; (9) fusion of two or more cells; and (10) movement of molecules through a tissue such as but not limited to skin blood vessels, endothelial linings, cardiac muscle, smooth muscle, and skeletal muscle.

For the purposes of this invention electrical treatment is defined as including the application of direct current or alternating current in any form such as, but not limited to, pulsed DC current or pulses AC current. In addition, different waveforms can be applied as pulsed DC or AC current such as but not limited to rectangular, square, triangular, sawtooth, exponentially increasing, or exponentially decreasing.

It may be appreciated by one of skill in the art that biological cells exist in many forms and in many types. The devices and methods described in this document apply to all types of living cells including prokaryotes, eukaryotes, and plant cells. Therefore, the term cell is to be broadly interpreted. In addition, the term cell also includes artificial cells such as liposomes and micelles for the purposes of this document as the methods and devices described can be applied to these entities also. The term "cell" in the description above and in the claims also has additional meaning which encompasses a single cell, cells in culture, cell aggregates, and/or a cell that is part of a tissue.

The term molecule has been used throughout this document and is to be defined as any type of molecular species. The devices and methods described herein are particularly applicable to therapeutic drugs, proteins, nucleic acid sequences, and plasmid DNA but can by applied for the delivery of any type of molecule and prove particularly useful for facilitating the entry of molecules into cells where the cell membrane poses a barrier to entry of the molecule under typical physiologic conditions. In addition, the devices and methods are applicable for simultaneously affecting more than one type of molecule. And furthermore, the manipulation of these molecules and cells can be for the purposes of the enhancement of therapeutic molecules for the treatment of disease or for the prevention (such as vaccine) of disease. The devices and methods described herein can be applied to any tissue type, either in vivo or in vitro. Applications will include both the treatment of humans and veterinary applications for the treatment of animals. In addition to the use of this for combating disease, the instant invention can be used for research purposes. The devices and methods described herein can be used for diagnostic and/or molecular identification purposes. For instance, a molecule comprising a marker or tag can be delivered to a targeted tissue and localization of the tagged molecule can be determined by any appropriate methodology.

In the foregoing description, certain terms have been used for brevity, clarity and understanding, but no unnecessary limitations are to be implied there from beyond the requirements of the prior art, because such words are used for description purposes herein and are intended to be broadly construed. Moreover, the embodiments of the apparatus illustrated and described herein are by way of example, and the scope of the invention is not limited to the exact details of construction.

The disclosure of all publications cited above are expressly incorporated herein by reference, each in its entirety, to the same extent as if each were incorporated by reference individually.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. An electroporation device comprising:
   an elongate tubular body having a proximal end, a distal tip, an inner wall, and an outer wall;
   a collar electrode having a central aperture disposed therein and fixedly attached to the distal tip of the tubular body wherein the collar electrode covers the entire surface of the distal tip;
   at least one tubular guide disposed within the elongate tubular body wherein the guide has a distal end, a proximal end, and an inner lumen; and
   at least one retractable needle disposed within the lumen of the at least one guide wherein the needle may extend through the central aperture of the collar electrode to contact a tissue;
   wherein the at least one needle and the collar electrode are independently addressable by a source of electricity;
   wherein the at least one guide is comprised of a conductive material;
   whereby a first agent is delivered to a tissue through the distal end of the at least one guide.

2. The device of claim 1, wherein the at least one retractable needle has a distal and a proximal end.

3. The device of claim 2, wherein the at least one needle is hollow.

4. The device of claim 3, wherein an aperture is positioned in the distal end of the at least one retractable needle whereby a second agent is delivered to the tissue through the aperture in the needle.

5. The device of claim 2, wherein the at least one needle is comprised of a conductive material.

6. The device of claim 5, wherein the proximal end of the at least one needle comprises a connector to couple the at least one needle to an electrical source.

7. The device of claim 1, wherein area between the inner wall of the elongate tubular body and the guide defines an interior space.

8. The device of claim 7, wherein the interior space is comprised of a non-conductive material.

9. The device of claim 1, wherein the proximal end of the tubular body comprises a connector to connect the device to an instrument selected from the group consisting of a catheter, an endoscope, and a bronchoscope.

10. The device of claim 1, wherein the proximal end of the tubular body comprises a connector to connect the device to a handle or probe for surgical treatment.

11. The device of claim 1, wherein the collar electrode is divided into a plurality of electrode segments separated by electrical insulation wherein each of the electrode segments is independently addressable to an electrical source.

12. The device of claim 11, wherein the plurality of electrode segments are spaced apart from each other by a predetermined space.

13. An electroporation device comprising:
    at least one guide having a distal tip and a proximal end wherein the guide has an elongate tubular body defining an inner lumen;
    a collar electrode having a central aperture disposed therein and fixedly attached to the distal tip of the at least one guide wherein the collar electrode covers the surface of the distal tip of the at least one guide; and
    at least one retractable needle disposed within the lumen of the at least one guide wherein the needle may extend through the central aperture of the collar electrode to contact a tissue;
    wherein the at least one needle and the collar electrode are independently addressable by a source of electricity;
    wherein the at least one guide is comprised of a conductive material;
    whereby a first agent is delivered to a tissue through the distal end of the at least one guide;
    wherein in a cross section of the electroporation device the collar electrode and the guide radially overlap.

14. The device of claim 13, wherein the at least one retractable needle has a distal and a proximal end.

15. The device of claim 14, wherein the at least one needle is hollow.

16. The device of claim 15, wherein an aperture is positioned in the distal end of the at least one retractable needle whereby a second agent is delivered to a tissue through the aperture in the needle.

17. The device of claim 13, wherein the at least one needle is comprised of a conductive material.

18. The device of claim 17, wherein the proximal end of the at least one needle comprises a connector to couple the at least one needle to an electrical source.

19. The device of claim 13, wherein the proximal end of the guide comprises a connector to connect the device to an instrument selected from the group consisting of a catheter, an endoscope, and a bronchoscope.

20. The device of claim 13, wherein the proximal end of the guide comprises a connector to connect the device to a handle or probe for surgical treatment.

21. The device of claim 13, wherein the collar electrode is divided into a plurality of electrode segments separated by electrical insulation wherein each of the electrode segments is independently addressable to an electrical source.

22. The device of claim 21, wherein the plurality of electrode segments are spaced apart from each other by a predetermined space.

* * * * *